US008343558B2

(12) United States Patent
Yomo et al.

(10) Patent No.: US 8,343,558 B2
(45) Date of Patent: *Jan. 1, 2013

(54) MICROORGANISM AND METHOD OF PROCESSING GREEN COFFEE BEANS USING THE SAME

(75) Inventors: Hideko Yomo, Toyonaka (JP); Toshiharu Nakajima, Ibaraki (JP); Takeshi Yonezawa, Ashiya (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 405 days.

This patent is subject to a terminal disclaimer.

(21) Appl. No.: 11/886,787

(22) PCT Filed: Mar. 24, 2006

(86) PCT No.: PCT/JP2006/305965
§ 371 (c)(1),
(2), (4) Date: May 28, 2008

(87) PCT Pub. No.: WO2006/101195
PCT Pub. Date: Sep. 28, 2006

(65) Prior Publication Data
US 2009/0226568 A1    Sep. 10, 2009

(30) Foreign Application Priority Data
Mar. 24, 2005    (JP) .................................. 2005-086884

(51) Int. Cl.
*A23G 1/02*    (2006.01)
(52) U.S. Cl. ........................... 426/45; 426/461; 426/594
(58) Field of Classification Search ................. 435/254.1
See application file for complete search history.

(56) References Cited

U.S. PATENT DOCUMENTS

| | | | |
|---|---|---|---|
| 1,313,209 | A | 8/1919 | Robison |
| 1,376,870 | A | 5/1921 | Graff et al. |
| 2,321,148 | A | 6/1943 | Kirby et al. |
| 2,341,724 | A | 2/1944 | Daniel |
| 2,526,872 | A | 10/1950 | Johnston et al. |
| 2,607,690 | A | 8/1952 | Johnston et al. |
| 3,153,377 | A | 10/1964 | Bosak |
| 3,373,041 | A | 3/1968 | Bloom et al. |
| 4,161,549 | A | 7/1979 | Ohno |
| 4,278,696 | A | 7/1981 | Magnolato |
| 4,388,341 | A | 6/1983 | Seto et al. |
| 4,867,992 | A * | 9/1989 | Boniello et al. ................ 426/45 |
| 4,976,983 | A | 12/1990 | Hirsh et al. |
| 5,132,134 | A | 7/1992 | Nini et al. |
| 5,267,507 | A | 12/1993 | Enomoto |
| 5,773,065 | A | 6/1998 | Clauzure |
| 5,776,525 | A | 7/1998 | Ide et al. |
| 6,054,162 | A | 4/2000 | Bradbury et al. |
| 6,482,959 | B1 | 11/2002 | Baloghne et al. |
| 6,660,322 | B2 | 12/2003 | Zapp et al. |
| 2004/0005381 | A1 | 1/2004 | Okada |
| 2004/0180112 | A1 | 9/2004 | Hagiwara |
| 2005/0084566 | A1 | 4/2005 | Bavan |
| 2005/0129827 | A1 | 6/2005 | Miljkovic et al. |
| 2007/0190207 | A1 | 8/2007 | Takahashi et al. |
| 2009/0104309 | A1 | 4/2009 | Nakajima et al. |
| 2009/0104310 | A1 | 4/2009 | Nakajima et al. |
| 2009/0130259 | A1 | 5/2009 | Yomo et al. |
| 2009/0226568 | A1 | 9/2009 | Yomo et al. |
| 2010/0143539 | A1 | 6/2010 | Minami et al. |

FOREIGN PATENT DOCUMENTS

| | | |
|---|---|---|
| EP | 0 282 762 A2 | 2/1988 |
| EP | 0837126 A2 | 4/1998 |
| EP | 1 695 631 A1 | 8/2006 |
| EP | 1880614 A1 | 1/2008 |
| JP | 50088267 A | 7/1975 |
| JP | 51-7147 | 1/1976 |
| JP | 51012969 A | 1/1976 |
| JP | 1-112950 | 5/1989 |
| JP | 4023992 A | 1/1992 |
| JP | 4-278072 | 10/1992 |
| JP | 5161488 A | 6/1993 |
| JP | 6-343390 | 12/1994 |
| JP | 9-502099 | 3/1997 |
| JP | 10-113163 | 5/1998 |
| JP | 11009190 A | 1/1999 |
| JP | 11043390 A | 2/1999 |
| JP | 11-319789 | 11/1999 |
| JP | 2001-178431 | 7/2001 |
| JP | 2003146897 A | 5/2003 |
| JP | 2004081053 A | 3/2004 |
| WO | WO 2005/029969 A1 | 4/2005 |

(Continued)

OTHER PUBLICATIONS

Suarez-Quiroz et al. (2004), International J. Food Science and Technology, 39, 501-507 (Published online Apr. 27, 2004).*
Pastore et al. [(Apr. 1994), Biotechnology Letters, 16(4): 389-392].*
International Search Report dated Jun. 20, 2006 for PCT/JP2006/305965 filed Mar. 24, 2006.
International Preliminary Report on Patentability and Written Opinion issued Aug. 21, 2008, for PCT/JP2006/305965 filed Mar. 24, 2006.
Joyeux et al., "Evolution of Acetic Acid Bacteria During Fermentation and Storage of Wine." Applied and Environmental Microbiology, vol. 48, No. 1, Jul. 1984, pp. 153-156.
Yoshihito Hikawa et al., "Enological Characteristics of Various Wine Making Yeasts", Report of the Yamanashi Industrial Technology Center, 2004, No. 18, pp. 141-144.

(Continued)

*Primary Examiner* — Tekchand Saidha
(74) *Attorney, Agent, or Firm* — Drinker Biddle & Reath LLP

(57) ABSTRACT

There is provided a novel microorganism capable of fermentation without placing particular limitations on fermentation conditions, as well as a method of processing green coffee beans using the novel microorganism, the method adding new, high-quality flavor and aroma to a coffee beverage by a simple operation, without instigating a particular increase in raw material costs and without requiring a new processing step.

The method for processing green coffee beans includes a fermentation step of bringing nutritive substances and microorganisms into contact with one another and causing fermentation in the presence of green coffee beans, wherein the microorganism used in the fermentation step is a microorganism belonging to the genus *Geotrichum*.

6 Claims, No Drawings

FOREIGN PATENT DOCUMENTS

| WO | WO-2006101195 A1 | 9/2006 |
| WO | WO-2006101196 A1 | 9/2006 |
| WO | WO-2006126587 A1 | 11/2006 |
| WO | WO-2006126588 A1 | 11/2006 |
| WO | WO-2008062886 A1 | 5/2008 |

OTHER PUBLICATIONS

L. Eduardo Betancourt et al., "Bedingungen Des Mikrobiellen Verderbs Von Grunem Kaffee. 1. Mitteilung: Sorptionsverhalten and SchimmelBildung", Deutsche LebensmittelRundschau, 1983, vol. 79, No. 11, pp. 366-369.

S. Avallone et al., "Fate of Mucilage Cell Wall Polysaccharides During Coffee Fermentation", J. Agric. Food Chem., 2001, vol. 49, pp. 5556-5559, Published by American Chemical Society Oct. 10, 2001.

Michitaka Naito et al., "Anti-Atherogenic Effects of Fermented Fresh Coffee Bean, Soybean and Rice Bran Extracts", Food Sci. Technol. Res., 2003, vol. 9, No. 2, pp. 170-175.

Daigle, P. et al., 1999, Production of aroma compounds by *Geotrichum candidum* on waste bread crumb, Food Microbiol., 1999, 16, pp. 517-522.

M. Sivetz et al., "Fruit—Green, Roast, and Soluble Coffee," Coffee Processing Technology, pp. 48-49, The Avi Publishing Company, Inc., Westport, Connecticut, (1963).

Roussos S. et al., "RintenhnnInginal management of coffee pulp—isolation, screening, characterization, selection of caffeine-degrading fungi and natural microflora present in coffee pulp husk," Appl. Microbiol. Biotechnol., 1995, vol. 42, pp. 756-762.

European Office Action issued May 7, 2010, in EP 06 746 785.2.

Extended European Search Report issued in European Application No. EP 06729914.9 mailed May 8, 2009.

International Search Report dated Aug. 1, 2006 for PCT/JP2006/310352 filed May 24, 2006.

Supplemental European Search Report and European Search Opinion issued May 27, 2009, in European Application No. EP 06746786.0.

International Preliminary Report on Patentability and Written Opinion issued Sep. 18, 2008, in International Application No. PCT/JP2006/310353 filed May 24, 2006.

International Preliminary Report on Patentability and Translation of Written Opinion mailed Nov. 29, 2007 in PCT International Application No. PCT/JP2006/310352, filed May 24, 2006.

International Search Report mailed Feb. 25, 2008 in PCT International Application No. PCT/JP2007/072701, filed Nov. 16, 2007.

English language translation of Hikawa et al., "Enological Characteristics of Various Wine Making Yeasts," Report of the Yamanashi Industrial Technology Center, 2004, No. 18, pp. 141-144.

Computer Translation of PCT International Publication No. WO 2005/029969 A1, published Apr. 7, 2005.

Lentner et al., "Organic acids in coffee in relation to the degree of roast," Journal of Food Science vol. 24, Issue 5, pp. 483-492 (1959).

Avallone et al., "Microbiological and Biochemical Study of Coffee Fermentation," Current Microbiology, 2001, pp. 252-256, vol. 42, Springer-Verlag.

Agate et al., "Role of Pectinolytic Yeasts in the Degradation of Mucilage Layer of *Coffea Robusta* Cherries," Applied Microbiology, Mar. 1966; pp. 256-260, vol. 14, No. 2, American Society for Microbiology.

International Preliminary Report on Patentability and Translation of Written Opinion mailed Aug. 12, 2008 in PCT International Application No. PCT/JP2006/305966, filed Mar. 24, 2006.

International Search Report mailed Aug. 1, 2006 in PCT International Application No. PCT/JP2006/310353, filed May 24, 2006.

International Preliminary Report on Patentability dated Jun. 26, 2006, including Translation of Written Opinion, in PCT International Application No. PCT/JP2004/013793, filed Sep. 22, 2004.

International Search Report mailed Dec. 28, 2004 in PCT International Application No. PCT/JP2004/013793, filed Sep. 22, 2004.

International Search Report mailed Jun. 20, 2006 in PCT International Application No. PCT/JP2006/305966, filed Mar. 24, 2006.

International Preliminary Report on Patentability and Written Opinion dated May 26, 2009 in PCT International Application No. PCT/JP2007/072701, filed Nov. 16, 2007.

* cited by examiner

SEQUENCE LISTING

```
<160> NUMBER OF SEQ ID NOS: 2

<210> SEQ ID NO 1
<211> LENGTH: 380
<212> TYPE: DNA
<213> ORGANISM: Geotrichum sp.
<220> FEATURE:
<221> NAME/KEY: gene
<222> LOCATION: (1)..(380)
<223> OTHER INFORMATION: 18SrDNA ITS4

<400> SEQUENCE: 1
attaagttca gcgggtaatc ctacttgatc tgaggttgaa tagtgttgtt tttcaaacga      60
atttgattcg atatatttta gaaaagcaat gcaattccaa gagagaaaca acgctcaaac     120
aagtatactt tgggggatac cccaaagtgc aatgtgcgtt caaaaactga tgattcactt     180
ctgcaattca caagaaatat cgcgtttcgc tgcgttcttc atcgatacga gaaccaagag     240
atccattgtt aaaagttttg attattttg ttttgactgt ataattattg tttgctgtgt     300
aaatttcaca aatatttata attcttaatg atccttccgc aggttcacct acggaaacct     360
tgttacgact tttaccttcc                                                380

<210> SEQ ID NO 2
<211> LENGTH: 381
<212> TYPE: DNA
<213> ORGANISM: Geotrichum sp.
<220> FEATURE:
<221> NAME/KEY: gene
<222> LOCATION: (1)..(381)
<223> OTHER INFORMATION: 18SrDNA ITS5

<400> SEQUENCE: 2
tttccgtagg tgaacctgcg gaaggatcat taagaattag taaatatttg tgaaatttac      60
acagcaaaca ataattctta cagtcaaaac aaaaataatc aaaactttta acaatggatc     120
tcttggttct cgtatcgatg aagaacgcag cgaaacgcga tatttcttgt gaattgcaga     180
agtgaatcat cagttttga acgcacattg cactttgggg tatcccccaa agtatacttg     240
tttgagcgtt gtttctctct tggaattgca ttgcttttct aaaatttcga atcaaattcg     300
tttgaaaaac aacactattc aacctcagat caagtaggat tacccgctga acttaagcat     360
atcaataagc gggaggaaca t                                              381
```

MICROORGANISM AND METHOD OF PROCESSING GREEN COFFEE BEANS USING THE SAME

CROSS REFERENCE TO RELATED APPLICATIONS

This application is the National Stage of International Application No. PCT/JP2006/305965 filed Mar. 24, 2006, and claims benefit of Japanese Application No. 2005-086884 filed Mar. 24, 2005, both of which are herein incorporated by reference in their entirety.

REFERENCE TO A SEQUENCE LISTING

A Sequence Listing containing SEQ ID NOS: 1-2 is incorporated herein by reference.

TECHNICAL FIELD

The present invention relates to a method for processing green coffee beans including a fermentation step of bringing nutritive substances and microorganisms into contact with one another and causing fermentation in the presence of green coffee beans.

BACKGROUND ART

At present, demand for coffee beverages as pleasure beverages continues to rise, and consumer tastes are diversifying with regard to coffee flavor and aroma.

A method of creating coffee bean roasts having a variety of differing degrees of roasting (from light roasts to Italian roasts) is generally employed as a method for creating diverse coffee flavors and aromas in order to respond to such consumer needs. However, a method of imparting coffee flavor and aroma by causing fermentation to be performed by microorganisms has furthermore been disclosed (see patent reference 1).

The method described in patent reference 1 utilizes the microorganism *Aspergillus oryzae*. Specifically, ground green coffee beans (nutritive substances) are inoculated with and fermented by *A. oryzae* and then roasted, and the coffee flavor and aroma components generated at this time are extracted. The extracted coffee flavor and aroma components are then added to coffee products such as coffee extract, roasted coffee beans, ground coffee, and the like, thereby enhancing the coffee flavor and aroma.

Patent Reference 1: JP H1-112950A

DISCLOSURE OF INVENTION

Problem to be Solved by the Invention

However, in the aforementioned method of patent reference 1, which utilizes *A. oryzae*, it is necessary to place a degree of limitation on the fermentation conditions when carrying out fermentation using *A. oryzae*. This is also mentioned in the specification of patent reference 1. For example, fermentation progresses slowly with green coffee beans of a normal grain size; therefore, in order to increase the speed of fermentation, it is necessary to finely grind the green coffee beans (thereby increasing the surface area that comes in contact with *A. oryzae*), and it is further necessary to culture the *A. oryzae* using a culture (fermentation) solution with a pH of 3.0 to 6.5.

Moreover, in this conventional method, a new processing step, in which the generated coffee flavor and aroma components are extracted and the extract is added to the aforementioned coffee product, is necessary in addition to the normal coffee beverage production step; therefore, in addition to requiring more time and effort, additional green coffee beans (in a ground state) are required for inoculation with and fermentation by the *A. oryzae*, which gives rise to a problem in that raw material costs are increased. Note that this conventional method is a method for enhancing the coffee flavor and aroma, and does not disclose a method for creating new coffee flavors and aromas.

Having been conceived in light of the aforementioned situation, the present invention provides a novel microorganism capable of fermentation without placing particular limitations on fermentation conditions, as well as a method of processing green coffee beans using the novel microorganism, the method being capable of adding new, high-quality flavor and aroma to a coffee beverage by a simple operation, without instigating a particular increase in raw material costs and without requiring a new processing step.

Means for Solving Problem (Configuration 1)

A first characteristic configuration of the present invention is a method for processing green coffee beans including a fermentation step of bringing nutritive substances and microorganisms into contact with one another and causing fermentation in the presence of green coffee beans, wherein the microorganism used in the fermentation step is a microorganism belonging to the genus *Geotrichum*.

(Configuration 2) According to a second characteristic configuration of the present invention, the microorganisms belonging to the genus *Geotrichum* are selected from among a group consisting of *Geotrichum candidum*, *Geotrichum rectangulatum*, and *Geotrichum klebahnii*.

(Configuration 3) According to a third characteristic of the present invention, the microorganism belonging to the genus *Geotrichum* is a new strain, a mutation thereof, or a transformant of the new strain or the mutation, of the *Geotrichum* sp. having the international deposit number FERM BP-10300.

(Configuration 4)

According to a fourth characteristic configuration of the present invention, the fermentation step is a step allowing a microorganism to perform a fermentation process in the presence of coffee cherries.

(Configuration 5)

According to a fifth characteristic configuration of the present invention, the fermentation process is carried out bringing the microorganism into direct contact with the coffee cherries.

(Configuration 6)

A sixth characteristic configuration of the present invention is green coffee beans obtained through the method according to one of claims 1 to 5.

(Configuration 7)

A seventh characteristic configuration of the present invention is roasted coffee beans obtained by performing a roasting process on the green coffee beans according to claim 6.

(Configuration 8)

An eighth characteristic configuration of the present invention is a coffee beverage obtained using the roasted coffee beans according to claim 3 as a raw material.

(Configuration 9)

A ninth characteristic configuration of the present invention is a new strain, a mutation thereof, or a transformant of the new strain or the mutation, of the *Geotrichum* sp. having the international deposit number FERM BP-10300.

Effects of the Invention

According to the method for processing green coffee beans according to the first characteristic configuration of the present invention, new flavor and aroma components can be added to green coffee beans with ease by a simple operation.

Green coffee beans have the property of absorbing water in preparation for germination, whereas some microorganisms such as yeast are known for decomposing (fermenting) organic compounds (nutritive substances), thereby producing alcohols, organic acids, and esters (referred to hereinafter as "fermentation components").

Accordingly, when nutritive substances and microorganisms are brought into contact with one another and cause fermentation in the presence of green coffee beans, the fermentation components that are produced thereby can be absorbed by the green coffee beans along with water. As a result, by roasting the green coffee beans obtained in this manner, it is possible to obtain roasted coffee beans that include new flavor and aroma components (fermentation components) produced through the fermentation in addition to the conventional coffee flavor and aroma components produced through a roasting process; accordingly, new flavor and aroma components can be added to a coffee beverage extracted from these roasted coffee beans.

Furthermore, utilizing microorganisms belonging to the genus *Geotrichum* in the fermentation process is a characteristic of the present invention. With this microorganism, the green coffee beans do not need to be ground at the time of fermentation, and green coffee beans of a normal grain size can be used, as opposed to the conventional technique, in which *Aspergillus oryzae* is utilized. In addition, there is no particular limitation placed on the fermentation (culture) conditions (the pH of the culture solution, the temperature, and the like), and thus the fermentation process can be carried out under normal, comparatively simple fermentation conditions (for example, coffee cherries (green coffee beans and coffee pulp (nutritive substances) are covered by the husk) and the microorganisms are submerged and mixed in a fermentation vat filled with water and fermented at 20-30° C., or the like). Therefore, according to the present invention, new flavor and aroma components can be added to green coffee beans with ease by a simple operation.

In the case of using *Geotrichum candidum*, *Geotrichum rectangulatum*, or *Geotrichum klebahnii* of the genus *Geotrichum*, as in the method for processing green coffee beans according to a second characteristic configuration of the present invention, it is possible to impart new flavor and aroma components (fermentation components) to the green coffee beans regardless of which microorganism is used. In particular, by using green coffee beans obtained when using the stated microorganisms as the raw materials, it is possible to obtain roasted coffee beans (or a coffee beverage) having a fruity, rich estery aroma that strikes a balance with conventional coffee beans produced through a roasting process (alcohol odors are suppressed).

A microorganism with the international deposit number FERM BP-10300, which is used in the method for processing green coffee beans according to a third characteristic configuration of the present invention, is a new strain of the *Geotrichum* sp. isolated from coffee cherries by the present inventors. By using this new strain, new flavor and aroma components (fermentation components) can be imparted to green coffee beans, making it possible to obtain roasted coffee beans (or a coffee beverage) having a more fruity, rich estery aroma. It should be noted that in the present invention, it is possible to use the new strain or a mutation thereof, or transformants of a mutation, as appropriate. A more highly fermentative strain (or, a strain having characteristics such as being easy to handle or the like) can be isolated from a mutation, a transformant, or the like, and utilized. Here, an induced (processed by radiation, a mutagen, or the like) spontaneous mutation or artificial mutation can be given as a mutation, whereas an exogenous gene being introduced into the new strain or mutation thereof can be given as a transformant.

"Coffee cherries" in the method for processing green coffee beans according to a fourth characteristic configuration of the present invention refers to the fruit of the *Coffea* plants of the family Rubiaceae, which is generally made up of a green coffee bean in the middle, coffee pulp surrounding the green coffee bean, and a husk surrounding the coffee pulp.

In the present invention, the coffee pulp contained within the coffee cherries (the part containing sugars and other nutrients) is primarily used as the nutritive substances. Therefore, extraneous nutritive substances need not be prepared, and thus worries of expansive raw material costs are avoided.

Furthermore, the present invention can be executed during the refining process where the green coffee beans are separated from the coffee cherries and collected. Therefore, as opposed to the conventional art, it is not necessary to provide a new processing step for extracting and adding coffee flavor and aroma components; the new flavors and aromas can be added to the green coffee beans easily.

In the method for processing green coffee beans according to a fifth characteristic configuration of the present invention, a method that brings microorganisms into direct contact with the coffee cherries (nutritive substances) (a direct contact method) is used in the fermentation process. Here, because the green coffee beans are in the immediate vicinity, the fermentation components such as alcohols, esters, and the like produced through fermentation can be quickly transferred to the green coffee beans.

Green coffee beans according to a sixth characteristic configuration of the present invention include new flavor and aroma components (fermentation components) produced through fermentation caused by microorganisms belonging to the genus *Geotrichum*.

Roasted coffee beans according to a seventh characteristic configuration of the present invention include new flavor and aroma components (fermentation components) produced through fermentation caused by microorganisms belonging to the genus *Geotrichum*, in addition to conventional coffee flavor and aroma components produced in the roasting process.

A coffee beverage according to an eighth characteristic configuration of the present invention features a full-bodied, complex flavor in which a high-quality aroma (a fruity, rich estery aroma that strikes a balance with conventional coffee beans produced through a roasting process (in which alcohol odors are suppressed)) has been added to the coffee beverage. This high-quality aroma is derived from new flavor and aroma components (fermentation components) produced through fermentation caused by microorganisms belonging to the genus *Geotrichum*, in addition to conventional coffee flavor and aroma components produced in the roasting process.

A microorganism having the international deposit number FERM BP-10300 according to a ninth characteristic configuration of the present invention, is a new strain of the *Geotrichum* sp. isolated from coffee cherries by the present inventors. New flavor and aroma components (fermentation components) can be imparted to green coffee beans by bringing the new strain of the present invention into contact with appropriate nutritive substances and causing fermentation thereby in the presence of the green coffee beans. It should be noted that in the present invention, it is possible to use the new strain or a mutation thereof, or transformants of these. A mutation according to the present invention may be, for example, a spontaneous mutation strain, or may be obtained by artificially inducing a mutation (through processing by radiation, a mutagen, or the like). In addition, a transformant can be obtained by introducing an expression vector incorporating an exogenous gene to the new strain or mutation thereof through a standard method.

BEST MODE FOR CARRYING OUT THE INVENTION

An embodiment of the present invention shall be described hereinafter.

An embodiment of the present invention shall be described hereinafter.

Embodiment

Microorganisms

The microorganisms that can be used in the present invention are microorganisms belonging to the genus *Geotrichum*. Preferably, *Geotrichum candidum, Geotrichum rectangulatum*, or *Geotrichum klebahnii* are used; even more preferably, a new strain (SAM 2421) of the *Geotrichum* sp., which has the international deposit number FERM BP-10300, a mutation thereof, or a transformant of these is used.

The microorganisms belonging to the genus *Geotrichum* in the present invention can be isolated from sources such as soil, vegetation, air, textiles, wood, house dust, animal fodder, rivers, silage, food products, fruits, grains, fertilizers, industrial waste, compost, excrement, digestive tracts, or the like; however, fruits (coffee cherries) are the preferable source.

A method in which coffee cherries are agitated in sterile water, the supernatant fluid thereof is applied on an agar medium containing proper antibiotics and cultured, and the colony that develops is isolated can be given as an example of an isolation method. However, it is also possible to purchase the microorganisms directly from an appropriate microbiological institution.

Note that "mutation" as referred to in the present invention includes spontaneous mutations, as well as artificially-induced mutations (processed by radiation, a mutagen, or the like), and has an altered DNA sequence as compared to a wild strain (a new strain (SAM 2421) of the *Geotrichum* sp. having the international deposit number FERM BP-10300).

(1) Spontaneous Mutation

A mutation occurring in a microorganism growing normally in a normal environment is called a "spontaneous mutation". Errors during DNA replication and intrinsic mutagens (nucleotide analogs) are considered the main causes of spontaneous mutations (Maki, "Spontaneous Mutagenesis and Recovery Mechanisms"; Cellular Engineering, Vol. 13, No. 8, pp. 663-672; 1994).

(2) Artificial Mutation 2-1. Processing by Radiation, Mutagens, or the Like

DNA is damaged when processed by radiation such as ultra-violet rays and X-rays, and when processed by artificial mutagens such as alkylating agents. This damage is fixed in the process of DNA replication to cause a mutation.

2-2. Polymerase Chain Reaction (PCR) Method

Because the PCR method amplifies DNA within a test tube, part of an intracellular mutation suppressing mechanism is missing, making it possible to induce mutations at high frequency. By combining this with a gene shuffling method (Stemmer, "Rapid Evolution of a Protein in Vitro by DNA Shuffling"; Nature, Vol. 370. pp. 389-391; August 1994), buildup of harmful mutations can be avoided, and plural beneficial mutations can be accumulated in the DNA.

2-3. Use of Mutators

Due to mutation suppression mechanisms, the occurrence rate of spontaneous mutations is kept extremely low in almost all organisms. A plurality of stages, involving 10 or more types of genes, are present in these mutation suppression mechanisms. An organism in which one or more of these genes breaks down experiences mutations at high frequency, and is this called a "mutator". These genes are called "mutator genes" (Maki, "Spontaneous Mutagenesis and Recovery Mechanisms"; Cellular Engineering, Vol. 13, No. 8, pp. 663-672; 1994; and Horst et. al., "*Escherichia coli* Mutator Genes"; Trends in Microbiology, Vol. 7, No. 1, pp. 29-36; January 1999).

In addition, "transformants" as stated in the present invention refers to a microorganism expressed by artificially introducing an exogenous gene held by a different type of organism into the new strain of the present invention (a new strain of the *Geotrichum* sp. with the international deposit number FERM BP-10300) or into a mutation thereof. Regarding a process, for example, the exogenous gene is incorporated into an appropriate expression vector, and the expression vector is introduced through a publicly-known method such as electroporation, the calcium phosphate method, the liposome method, the DAEA-dextran method, and so on.

In the present invention, various flavors and aromas can be imparted by selecting the type, fermentation conditions, and so on of the microorganism belonging to the genus *Geotrichum*. Thus, microorganism strains that allow desired flavors and aromas to be added are appropriately selected and used.

There are no particular limitations regarding the amount of microorganism used in the present invention as long as the effect of adding flavor and aroma can be obtained and the amount of organism can be suitably set in view of the culture time and the cost. For example, a wet weight of approximately 1-100 mg per 100 g of green coffee beans is appropriate.

(Coffee Cherries)

"Coffee cherries" in the present invention refers to the fruit of the *Coffea* plant, which is made up of green coffee beans (seeds), pulp (the part including sugars and other nutrients), and a husk. To be more specific, the green coffee beans are innermost, surrounded by, in order, silverskin, parchment, pulp, and the husk. Coffee types that can be used include *Coffea arabica, Coffea robusta*, and *Coffea liberica*, and these can have been grown in Brazil, Ethiopia, Vietnam, and Guatemala, for example, although there is no particular limitation to these. It should be noted that undried and dried coffee cherries are used in this embodiment, and taking the specific gravity of a green coffee bean as 1, these have specific gravities of "coffee cherry (undried):dried coffee cherry:green coffee bean=6:4:1."

(Nutritive Substances)

Fruit, fruit juice, sugars, culture media, and the like can be given as examples of nutritive substances used in the fermentation process of the present invention; however, coffee pulp is preferable for use as the metabolite. It should be noted, however, that "coffee pulp" as stated in the present invention shall, for the sake of simplicity, refer to all parts of the coffee cherry (regardless of whether undried or dried) aside from the green coffee bean and husk thereof.

As coffee pulp, coffee cherries that have not undergone a refining process may be used, or alternatively, the pulp obtained when the green coffee beans are removed from the coffee cherries during the refining process may be used. In addition, the coffee pulp may be undried or dried. Note that the fruit pulp used is not limited to coffee pulp; it is possible to use other fruit pulps such as grape pulp, cherry pulp, and peach pulp as necessary. In addition, these fruit pulps, including coffee pulp, may be used alone or in arbitrary combinations.

The following can be given as examples of nutritive substances aside from the stated fruit pulps: fruit juice (from, for example, grapes, peaches, apples, and so on); sugars (for example, monosaccharides, disaccharides, and polysaccharides obtained from plants such as sugar cane and sweet potatoes); grains (for example, wort obtained from glycated wheat germ); and culture media. However, no particular limitation is placed on the components as long as they can be metabolized by the microorganisms, and these nutritive substances, including the fruit pulps, may be used along or in arbitrary combinations.

(Coffee Pulp Exposure Method)

In the case where the coffee cherries are taken as-is and the coffee pulp therein is used as the metabolite, a method of exposing at least part of the coffee pulp to the surface of the coffee cherries may be used in order to speed up fermentation.

As a method for exposing the coffee pulp, the harvested coffee cherries may be cut with a sharp blade, the coffee cherries may be pressurized using a threshing device or the like so that cuts appear in the husk, or the like; however, during such exposure, cuts are not inflicted on the green coffee beans within. Alternatively, a peeling machine may be used, removing only the husk of the coffee cherry and exposing the pulp thereby. Note that the abovementioned pulp exposure processing is not particularly necessary for coffee cherries in which at least part of the pulp has been exposed by cuts accidentally occurring during harvesting of the coffee cherries. Furthermore, the abovementioned pulp exposure processing is not particularly necessary in the case of using coffee pulp obtained when the green coffee beans are removed during the refining process; extra green coffee beans are added and fermentation is carried out.

(Fermentation Process)

1. Method of Bringing Microorganisms and Nutritive Substances into Contact

The method described hereinafter can be given as an example of a method for bringing microorganisms and nutritive substances into contact with one another during the fermentation process of the present invention.

(a) Direct Contact Method

The "direct contact method" is a method that brings microorganisms and nutritive substances into direct contact in the presence of green coffee beans. For example, microorganisms are sprayed or scattered upon coffee cherries having at least part of the coffee pulp exposed (or upon a mixture of coffee pulp and green coffee beans obtained when the green coffee beans are removed during the refining process), bringing the microorganisms into direct contact, and fermentation is caused thereby. In particular, when causing fermentation using coffee cherries in which part of the pulp is exposed, fermentation progresses efficiently due to metabolized sugars and the like being localized at high concentrations; in addition, because the green coffee beans are present in the immediate vicinity, fermentation components such as alcohols and esters produced through fermentation can be quickly transferred to the green coffee beans. Note that in the case where dried coffee cherries (or coffee pulp) are used, fermentation may be carried out in a state in which a moderate amount of water has been added to the cherries/pulp. Microorganisms belonging to the genus *Geotrichum* are well-suited to the direct contact method.

(b) Indirect Contact Method

The "indirect contact method" is a method in which a fermentation vat containing a fermentation solution is prepared, green coffee beans, nutritive substances, and microorganisms are added to the fermentation solution, and the microorganisms are caused to come into contact with the nutritive substances released into the fermentation solution. For example, microorganisms and coffee cherries having at least part of the coffee pulp exposed (or upon a mixture of coffee pulp and green coffee beans obtained when the green coffee beans are removed during the refining process) are added to the fermentation solution, and fermentation is caused thereby.

2. Fermentation Conditions

There are no particular limitations regarding the fermentation conditions of the microorganisms, as long as fermentation is carried out. Conditions suitable for fermentation (for example, the type and amount (initial number) of microorganisms used, type and amount (concentration) of metabolite, temperature, moisture content, pH, oxygen or carbon dioxide concentration, fermentation time, and so on) can be set as seen fit, as necessary. Additionally, for example, additives such as pH adjustors, commercially-available nutrient cultures for correcting nitrogen and carbon sources, and the like may be accessorily added, aside from the stated nutritive substances.

To prevent growth of other microorganisms (saprophytic bacteria) particularly in the fermentation process of the present invention, fermentation may be carried out while controlling conditions such as the temperature, pH, carbon concentration, and so on. For example, fermentation may be carried out in a low-temperature environment, the temperature being from 15 to 30° C., in which the growth of other saprophytic bacteria can be suppressed. Fermentation may also be carried out under pH conditions in which pH adjustors or the like (citric acid, malic acid, lactic acid, and so on) are added, thereby making it possible to suppress the growth of other saprophytic bacteria. Alternatively, fermentation may be carried out under more anaerobic (or aerobic) conditions in which the carbon dioxide concentration (or the oxygen concentration) is raised and the growth of saprophytic bacteria is suppressed thereby.

In addition, the fermentation process of the present invention can be carried out in a thermostatic chamber, tank, or storage chamber in which the stated fermentation conditions (for example, the type and amount (initial number) of microorganisms used, type and amount (concentration) of nutritive substances, temperature, moisture content, pH, oxygen or carbon dioxide concentration, fermentation time, and so on) can be automatically and/or manually controlled.

Note that there are no limitations regarding the time required for the fermentation process, and this can be suitably chosen based on the quality and strength of the flavor and aroma to be added or based on the microorganism or metabolite. It is also possible to end the fermentation process once the nutritive substances have been consumed.

The fermentation process can be ended through a combination of such methods as heat sterilization, water rinsing, sun-drying, separating the nutritive substances and green coffee beans, or roasting. For example, fermentation can be ended by using a drying machine to dry the product at 50 to 60° C. for about one to three days.

3. Fermentation Process Example

An example of fermentation using coffee cherries shall be described here.

First, the stated microorganisms are precultured and the suspension thereof is adjusted. Specifically, the microorganisms are aerobically cultured in an appropriate liquid culture medium; the post-culture culture solution is separated in a centrifuge, discarding the supernatant; and the pellets (microorganism masses) obtained thereby are suspended in sterile water.

Using the stated suspension, it is possible, for example, to perform the fermentation process during the process of preparing the green coffee beans.

Two types of refining processes for obtaining green coffee beans from coffee cherries are known: "Natural" and "Washed".

"Natural" is a method for obtaining green coffee beans that involves drying harvested green coffee cherries as they are, and after drying, the coffee cherries are husked to remove their pulp and skin, for example.

On the other hand, in "Washed", harvested coffee beans are soaked in a vat to remove impurities and the coffee pulp is removed by a pulp removing machine, after which the beans are submerged in water in a fermentation vat to dissolve any remnants on the seed, and after washing, they are dried and husked to remove the skin and the like to yield green coffee beans.

"Natural" process is easy to conduct, but it is mainly suited for areas with dry climates. On the other hand, "Washed" process is primarily suited for areas that are characterized by abundant rainfall.

First, for example, in "Natural" process, coffee cherries are harvested; their surfaces are cut with a knife or the like, thus partially exposing the coffee pulp; a microorganism suspension is applied thereupon using the abovementioned direct contact method; the microorganisms are brought into direct contact with the cherries and allowed to ferment; and after the fermentation, the cherries are dried.

In addition, for example, in "Washed" process, coffee cherries are harvested; their surfaces are cut with a knife or the like, thus partially exposing the coffee pulp; and when the cherries are submerged in a water-filled vat and impurities are removed therefrom, the microorganisms (suspension) are added to the water-filled vat (fermentation vat) along with the cherries, and allowed to ferment. Because the cherries are cut and the pulp is exposed, sugars (nutritive substances) within the pulp can easily be released into the vat, facilitating fermentation through the microorganisms. Alternatively, fermentation through the stated direct contact method or indirect contact method can be performed before submerging the harvested coffee cherries in the vat, or before the coffee pulp has been removed from the coffee cherries that have been submerged in the vat and had impurities removed.

Note that the pulp of coffee cherries still on the plant may be exposed prior to the coffee cherries being harvested, and fermentation accelerated through the stated direct contact method.

Coffee cherries for which the fermentation process has ended have the pulp removed through a normal refining process after having the microorganisms rinsed off and removed with water or with the microorganisms still attached. The cherries are then threshed and the green coffee beans removed (one or two coffee beans can be obtained from a single coffee cherry).

The green coffee beans removed in this manner can be roasted through a normal method, and various types of coffee beans that have been roasted to differing degrees (from light roasts to Italian roasts) can be obtained.

The roasted coffee beans that are obtained can be ground and soaked with water, which is then extracted through filtration by a filter; this can be taken as a regular coffee beverage, or it can be used as an industrial ingredient for instant coffee, coffee extract, canned coffee, or the like.

The present invention is described in specific detail in the following working examples; however, the invention is not limited to these working examples.

Working Example 1

Isolation and Identification of the SAM 2421 Strain

The SAM 2421 strain, which can be suitably used in the present invention, was isolated through the method described hereinafter.

Coffee cherries were tested as an isolation source of the microorganism. 5 coffee cherries (produced in Okinawa) and 5 ml of sterilized water were added to a test tube, and were agitated by a vortex mixer. Two concentrations, or the supernatant fluid as-is and a $1/1000^{th}$ dilution thereof, were applied onto a YM agar medium with 100 ppm chloramphenicol added. Five types of colonies were isolated after culturing for four days at 23° C. These five types of strains were aerobically cultured for three days at 27° C. using a YM culture medium or a red grape concentrate (mast). After the supernatant was discarded through centrifugal separation (3000 rpm for 10 minutes), the pellets of the stated five types of strains were suspended in water, and five types of suspensions were obtained thereby.

Five 5000 ml Erlenmeyer flasks were prepared. 1000 g of coffee cherries and 1000 mL of a diluent of each of the abovementioned suspensions (wherein 1 ml of each of the five types of suspension is diluted with water, resulting in 1000 mL of liquid) were combined in each Erlenmeyer flask and mixed. Fermentation was carried out in a thermostatic chamber with a room temperature of 23° C., the flasks being allowed to stand for 72 hours.

The post-fermentation coffee cherries were removed from the fermentation solution upon a characteristic flavor and aroma appearing in the fermentation solution, discarded, and then dried for 48 hours in a drier at 55° C.; after this, the pulp and husk was removed, and five types of green coffee beans were obtained thereby. 100 g of each of the types of green coffee beans obtained were roasted using a "deep roast" button of a fully-automatic household coffee bean roasting machine (CRPA-100, Tortoise Co. Ltd.). The roast time was approximately 25 minutes.

Sensory evaluation of the five types of roasted beans obtained and an extract thereof showed that one type had a particularly favorable aroma.

Accordingly, a BLAST homology search was carried out in the National Center for Biotechnology Information gene database (NCBI; http://www.ncbi.nlm.nih.gov) for a partial base sequence of an 18S rDNA gene (the ITS4 region and ITS5 region) of the strain that provided the particularly favorable aroma. The result showed 97% homology with *Galactomyces geotrichum* (Ascomycota) and 96% homology with *Geotrichum candidum*, which are registered in the database. Note that the sequenced ITS4 region and ITS5 region base sequences are respectively indicated by sequence numbers 1 and 2 in the following sequence list.

The following attributes of this strain was observed:

(1) Colony: white, colorless underside, non-choromophorous.

(2) Odor: strong fermentative odor, sour-sweet odor.

(3) Hypha: septate wall, colorless, becomes anthroconidium as hypha grows. Note that ascus could not be confirmed.

*Galactomyces* is the name of the perfect stage of this strain, and is classified into Ascomycota. For the stated isolated strain, Ascomycota was grown on a slide glass and observation of the ascus was attempted. However, because ascus could not be observed, it was determined that the strain belongs to the genus *Geotrichum*.

In this manner, the stated isolated strain was identified as a microorganism of the genus *Geotrichum* classified as a deuteromycete, designated as *Geotrichum* sp. SAM 2421, and deposited in the National Institute of Advanced Industrial Science and Technology's International Patent Organism Depository (deposit number FERM BP-10300).

Working Example 2

Using the *Geotrichum* strains (deuteromycetes) to which SAM 2421 obtained in working example 1 belongs, the effects of the fermentation process on green coffee beans were studied. The four types of strains used in the test are as follows:

(1) Newly isolated strain (SAM 2421) of the *Geotrichum* sp.

*Geotrichum candidum* (IAM 12700) of the same genus as the stated new strain, purchased from the Tokyo University Institute of Molecular and Cellular Biosciences.

(3) *Geotrichum rectangulatum* (JCM 1750), a related species of *Geotrichum candidum*.

(4) *Geotrichum klebahnii* (JCM 2171) purchased from the Japan Collection of Microorganisms.

As a control, the following were used: (5) wine yeast Lalvin (L 2323) purchased from the SCETI company, and (6) *Aspergillus niger*, a Koji used for the distilled liquor Koji known as shochu, classified as the same deuteromycete as *Geotrichum*.

These six types of strains were aerobically cultured for three days at 27° C. using a YM culture medium or a red grape concentrate (must). After the supernatant was discarded through centrifugal separation (3000 rpm for 10 minutes), the pellets of the stated six types of strains were suspended in water, and six types of suspensions were obtained thereby.

Six 5000 ml Erlenmeyer flasks were prepared. 1000 g of coffee cherries and 1000 mL of a diluent of each of the abovementioned suspensions (wherein 1 ml of each of the six types of suspension is diluted with water, resulting in 1000 mL of liquid) were combined in each Erlenmeyer flask and mixed. Fermentation was carried out in a thermostatic chamber with a room temperature of 23° C., the flasks being allowed to stand for 72 hours.

Hyphoid growth began on the surface of the cherry suspension as fermentation progressed, and formation of a film was observed. At the same time, characteristic aromas and flavors appeared in the fermentation solution.

The post-fermentation coffee cherries were removed from the fermentation solution, discarded, and then dried for 48 hours in a drier at 55° C.; after this, the pulp and husk was removed, and six types of green coffee beans were obtained thereby. 100 g of each of the types of green coffee beans obtained were roasted using a "deep roast" button of a fully-automatic household coffee bean roasting machine (CRPA-100, Tortoise Co. Ltd.). The roast time was approximately 25 minutes.

Next, sensory evaluation for the stated six roast types was performed by a panel of five coffee sensory evaluators. 30 g of each roasted coffee bean was placed in a dedicated sensory flask as-is, without being ground, and the glass was capped. The cap was removed at the time of evaluation, which was based on four criteria: brewing aroma, estery aroma, roast aroma, and alcohol odor. The roasted beans fermented with wine yeast were used as the control, with larger numbers being "strong" and smaller numbers being "weak", the evaluation being performed on a point scale of 1 to 5 in increments of 0.1. Table 1 shows the average values of the five assessors.

With the control using wine yeast, brewing aroma was strong, and a rather strong alcohol odor was present. However, in the case of the *Geotrichum* strains, a light estery aroma reminiscent of fresh fruit had been imparted, without off-flavors such as brewing aroma and alcohol odor. While strong aromas were obtained to a degree when using the related *Aspergillus*, the aroma lacked fruity, and a well-balanced coffee flavor was not obtained.

TABLE 1

Sensory Evaluation of Roasted Beans

| Evaluated Item | L2323 (wine yeast) | SAM 2421 | IAM 12700 | JCM 1750 | JCM 2171 | *Aspergillus* |
|---|---|---|---|---|---|---|
| Brewing Aroma | 3.0 | 2.0 | 2.0 | 2.0 | 2.0 | 2.5 |
| Estery Aroma | 3.0 | 4.8 | 4.5 | 4.4 | 4.0 | 2.8 |
| Roast Aroma | 3.0 | 3.0 | 3.0 | 3.0 | 3.0 | 3.0 |
| Alcohol Odor | Present | None | None | None | None | None |

Working Example 3

Evaluation of Aroma Components in Roasted Beans

Aroma components were analyzed using gas chromatography (GC). 5 g of each of the six types of unground roasted coffee beans obtained as described in working example 2 were placed as-is in GC sample tubes, and the headspace gas was analyzed. In addition to the test samples, Brazilian Santos beans (roasted beans) (No. 2) (called "Brazilian beans" in the following tables) were used for comparison of the analysis values. The devices used were an Agilent 7694 Headspace Sampler and an Agilent 6890 GC system. A sample was introduced at 60° C. over 15 minutes at a 10:1 split; the column used was a CP 7673wax (25 mm long×0.25 mm in diameter, and a thickness of 1.2 μm. The temperature was held at 40° C. for five minutes and then increased 10° C./min up to 220° C., then held at 220° C. for 20 minutes. MSD and FID were used as detectors.

Analysis results for ester and alcohol characteristic to the fermentation process are shown in table 2 below. While also being detected in the Brazilian Santos beans (roasted beans), methyl acetate, ethyl acetate, and ethanol were prominent in the samples in which fermentation was carried out using wine yeast and the *Geotrichum* strains. As can be seen by the considerable amounts of the three stated components, in the wine yeast sample, alcohol odor was strong, and brewing aroma was prevalent, and thus the balance was lost.

However, in the sample fermented using the *Geotrichum* strains, it can be seen that the peak considered to be related to brewing aroma, which was prominent in the wine yeast sample, has decreased, and that the component makeup is well-balanced. Methyl acetate was too strong when the related *Aspergillus* was used, which was considered to be a cause of poor aroma balance.

TABLE 2

GC Analysis Values of Roasted Beans

| Component name | L2323 (wine yeast) | SAM 2421 | IAM 12700 | JCM 1750 | JCM 2171 | *Aspergillus niger* | Brazilian |
|---|---|---|---|---|---|---|---|
| Methyl Acetate | 3232 | 1904 | 3699 | 1968 | 2668 | 5234 | 383 |
| Ethyl Acetate | 2967 | 946 | 1563 | 2507 | 1370 | 1648 | 32 |
| Ethanol | 6077 | 2141 | 2024 | 3220 | 1988 | 2148 | 280 |

(Unit: Picoampere/second)

Working Example 4

Sensory Evaluation of Coffee Extract

Coffee extract was produced using roasted beans of each of the stated six types obtained as described in working example 2. The respective coffee beans were finely ground; 100 g of hot water was added to 12 g of ground beans, and the mixture was agitated. Coffee that floated to the surface was removed and sensory evaluation was performed on the supernatant fluid, in accordance with the cup test standard method. This was performed by a panel of five coffee sensory evaluators. Five items were evaluated: aroma (brewing aroma, estery aroma, and alcohol odor) and taste (bitterness, body). The evaluation results are shown in Table 3. Wine yeast fermentation solution was used as a control. The control median was evaluated as 3, with larger numbers being "strong" and smaller numbers being "weak", the evaluation being performed on a point scale of 1 to 5 in increments of 0.1. Average values of evaluation points are shown.

Working Example 5

Aroma Components of Coffee Extract 10 ml of each extract obtained as described in working example 4 were placed in a GC sample tube and GC analysis performed thereon. Other analysis conditions were based on the aforementioned method of working example 3. The results are shown in Table 4.

In the same manner as the roasted beans in working example 3, the volatile amount of esters and ethanol was too high in the fermentation using wine yeast, which was considered to be a cause of a loss of balance and the presence of alcohol odor. However, the amounts of both of these were suppressed and balance improved when using *Geotrichum*. Amounts such as these do not interfere with other aroma components not listed here, and thus it is thought that excellent beans having a rich, fruity, coffee-like aroma can be produced.

TABLE 4

GC Analysis Values of Coffee Extract

| Component name | L2323 (wine yeast) | SAM 2421 | IAM 12700 | JCM 1750 | JCM 2171 | *Aspergillus niger* | Brazilian |
|---|---|---|---|---|---|---|---|
| Methyl Acetate | 7.1 | 2.7 | 3.7 | 6.4 | 2.8 | 2.2 | 1.0 |
| Ethyl Acetate | 1.9 | 0.5 | 1.8 | 2.7 | 0.5 | 0.3 | 0.1 |
| Ethanol | 58.9 | 20.4 | 39.8 | 75.1 | 18.1 | 9.5 | 5.5 |

(Unit: ppb)

From this, it can be seen that favorable aromas can be imparted in coffee beans by performing a fermentation process on green coffee beans using various *Geotrichum* bacteria belonging to SAM 2421.

Working Example 6

A test was carried out using commercially-available strains of *Geotrichum*.

4 strains, which are sold by Chr. Hansen for use as starters in cheese production, and which belong to *Geotrichum candidum*, were used: GEO CA (item no. 200691); GEO CB (item no. 200692); GEO CD1 (item no. 200693); and GEO CE (item no. 200835). Note that wine yeast (L2323) was used as a control.

0.1 g of each samples of five strains were measured out and suspended in water; this was further diluted with water to 1000 ml. 1000 mL of the diluent and 1000 g of coffee cherries were added to an Erlenmeyer flask (5000 ml) and fermentation commenced. Fermentation was carried out in a thermostatic chamber with a room temperature of 23° C., the flasks being allowed to stand for 72 hours. Hyphoid growth began on the surface of the cherry suspension as fermentation progressed, and formation of a film was observed. At the same time, characteristic aromas and flavors appeared in the fermentation solution.

TABLE 3

Sensory Evaluation of Coffee Extract

| Evaluated Item | | L2323 (wine yeast) | SAM 2421 | IAM 12700 | JCM 1750 | JCM 2171 | *Aspergillus* |
|---|---|---|---|---|---|---|---|
| Aroma | Brewing Aroma | 4.0 | 3.0 | 3.0 | 3.0 | 3.0 | 3.5 |
| | Estery Aroma | 3.0 | 4.0 | 3.7 | 3.8 | 3.2 | 2.5 |
| | Alcohol Odor | Present | None | None | None | None | None |
| Taste | Body | 2.5 | 3.5 | 3.4 | 3.1 | 3.2 | 2.5 |
| | Bitterness | 3.0 | 3.0 | 3.0 | 3.0 | 3.0 | 3.0 |

The post-fermentation coffee cherries were removed from the fermentation solution, discarded, and then dried for 48 hours in a drier at 55° C.; after this, the pulp and husk was removed, and five types of green coffee beans were obtained thereby. 100 g of each of the types of green coffee beans obtained were roasted using a "deep roast" button of a fully-automatic household coffee bean roasting machine (CRPA-100, Tortoise Co. Ltd.). The roast time was approximately 25 minutes. Next, sensory evaluation was performed based on the method described in working example 2 (table 5).

TABLE 5

| Evaluated Item | L2323 (wine yeast) | GEO CA | GEO CB | GEO CD1 | GEO CE |
|---|---|---|---|---|---|
| Brewing Aroma | 3.0 | 2.0 | 2.0 | 2.0 | 2.0 |
| Estery Aroma | 3.0 | 3.5 | 4.0 | 3.8 | 4.0 |
| Roast Aroma | 3.0 | 3.0 | 3.0 | 3.0 | 3.0 |
| Alcohol Odor | Present | None | None | None | None |

With the control using wine yeast, brewing aroma was strong, and a rather strong alcohol odor was present. However, in the case of the *Geotrichum* strains, a light estery aroma reminiscent of fresh fruit had been imparted, without off-flavors such as brewing aroma and alcohol odor.

Furthermore, coffee extract was produced using the respective roasted coffee beans. The respective coffee beans were finely ground; 100 g of hot water was added to 12 g of ground beans, and the mixture was agitated. Sensory evaluation was performed on the obtained coffee extract based on the method described in working example 4 (table 6).

TABLE 6

| Evaluated Item | | L2323 (wine yeast) | GEO CA | GEO CB | GEO CD1 | GEO CE |
|---|---|---|---|---|---|---|
| Aroma | Brewing Aroma | 4.0 | 3.0 | 3.0 | 3.0 | 3.0 |
| | Estery Aroma | 3.0 | 3.5 | 3.7 | 3.8 | 4.2 |
| | Alcohol Odor | Present | None | None | None | None |
| Taste | Body | 2.5 | 3.0 | 3.4 | 3.1 | 3.2 |
| | Bitterness | 3.0 | 3.0 | 3.0 | 3.0 | 3.0 |

Similarly to the abovementioned roasted beans, with the control using wine yeast, brewing aroma was strong, and a rather strong alcohol odor was present. However, in the case of the *Geotrichum* strains, a light estery aroma reminiscent of fresh fruit had been imparted, without off-flavors such as brewing aroma and alcohol odor. In terms of taste, a sense of body had been imparted in the roasted beans, as compared to the control.

From this, it can be seen that favorable aromas can be imparted in coffee beans by performing a fermentation process on green coffee beans using various *Geotrichum* bacteria that are commercially available.

Working Example 7

Fermentation was performed through the direct contact method using the SAM 2421 obtained as described in working example 1. SAM 2421 was aerobically cultured for three days at 27° C. using a red grape concentrate (mast). After the supernatant was discarded through centrifugal separation (3000 rpm for 10 minutes), a suspension of the pellets in water was prepared. 1000 g of coffee cherries were added to a 5000 ml flask; 20 ml of the suspension was applied thereupon; and the mixture was thoroughly agitated. This was covered with aluminum foil and allowed to ferment for three days at room temperature (23° C. to 30° C.). As fermentation progressed, a small amount of juice accumulated on the bottom. A white fluff of SAM 2421 was observed growing on the surface of the cherries, and the receptacle was filled with a fruity ferment flavor.

After fermentation, the coffee cherries were drained, and then dried for 48 hours in a drier at 55° C.; after this, the pulp and husk was removed, and green coffee beans were obtained thereby. 100 g of the green coffee beans obtained were roasted using a "deep roast" button of a fully-automatic household coffee bean roasting machine (CRPA-100, Tortoise Co. Ltd.). The roast time was approximately 25 minutes.

Sensory analysis was performed by a panel of five coffee sensory evaluators. 30 g of the roasted coffee beans was placed in a dedicated sensory flask as-is, without being ground, and the glass was capped. The cap was removed at the time of evaluation, which was based on four criteria: brewing aroma, estery aroma, roast aroma, and alcohol odor. Roasted coffee beans fermented through the indirect contact method using the SAM 2421 (roasted coffee beans obtained as described in working example 2) were used as a control. Larger numbers were "strong" and smaller numbers were "weak", the evaluation being performed on a point scale of 1 to 5 in increments of 0.1. Table 7 shows the results of the average values of the five assessors.

TABLE 7

| Evaluated Item | Indirect Contact Method (Control) | Direct Contact Method |
|---|---|---|
| Brewing Aroma | 3.0 | 3.0 |
| Estery Aroma | 3.0 | 4.8 |
| Roast Aroma | 3.0 | 3.0 |
| Alcohol Odor | None | None |

Furthermore, coffee extract was produced using the roasted coffee beans. The coffee beans were finely ground; 100 g of hot water was added to 12 g of ground beans, and the mixture was agitated. Coffee that floated to the surface was removed and sensory evaluation was performed on the supernatant fluid, in accordance with the cup test standard method. This was performed by a panel of five coffee sensory evaluators. Four items were evaluated: aroma (brewing aroma, estery aroma) and taste (bitterness, body). A coffee extract obtained from roasted coffee beans fermented through the indirect contact method using the SAM 2421 (a coffee extract obtained as described in working example 4) was used as a control. Larger numbers indicated "strong" and smaller numbers indicated "weak", the evaluation being performed on a point scale of 1 to 5 in increments of 0.1. Table 8 shows the results of the average values of the five assessors.

TABLE 8

| | Evaluated Item | Indirect Contact Method (Control) | Direct Contact Method |
|---|---|---|---|
| Aroma | Brewing Aroma | 3.0 | 3.0 |
| | Estery Aroma | 3.0 | 4.8 |
| | Alcohol Odor | None | None |
| Taste | Body | 3.0 | 4.5 |
| | Bitterness | 3.0 | 3.0 |

It can be seen, from the results shown in Tables 7 and 8, that excellent beans having a more rich, fruity, coffee-like aroma can be produced through the direct contact method, even compared to the controls shown in working examples 2 and 4, which showed favorable results.

The roasted coffee beans obtained were analyzed using gas chromatography based on the method described in working example 3. The results showed, in the roasted beans obtained through the direct contact method, a total peak area of 1.6 times that of the control obtained through the indirect contact method. When taken in consideration with the results of the sensory evaluation for the roasted beans and the coffee extract, it was confirmed that using the direct contact method allowed a favorable and high-quality aroma and taste to be efficiently imparted to the coffee beans without upsetting the balance thereof.

INDUSTRIAL APPLICABILITY

The present invention has exceptional utility in not only processing tasks such as refining and roasting coffee cherries, but also in the task of manufacturing coffee beverages by manufacturing various types of products (regular coffee, instant coffee, canned coffee, coffee aroma, etc.) from roasted coffee beans produced from green coffee beans that have been processed according to the invention, and can contribute to the further development of those industries.

The invention claimed is:

1. A method for processing green coffee beans comprising a fermentation step:
   bringing nutritive substances and an isolated microorganism into contact with one another at a temperature of 15 to 30° C. to perform fermentation in the presence of green coffee beans,
   wherein the isolated microorganism in the fermentation step is a microorganism belonging to the genus *Geotrichum*,
   wherein the fermentation step is carried out by bringing the isolated microorganism into direct contact with coffee cherries, and wherein the isolated microorganism belonging to the genus *Geotrichum* is selected from the group consisting of *Geotrichum candidum* (IAM 12700, GEO CA (item no. 200691), GEO CB (items no. 200692), GEO CD1 (item no. 200693), and GEO CE (item no. 200835)), *Geotrichum rectangulatum* (JCM 1750), *Geotrichum klebahnii* (JCM 2171), and a new strain of the *Geotrichum* sp. having the international deposit number FERM BP-10300.

2. Green coffee beans obtained by the method of claim 1.

3. Roasted coffee beans obtained by performing a roasting process on the green coffee beans according to claim 2.

4. A coffee beverage obtained by adding the roasted coffee beans according to claim 3 as a raw material.

5. A new isolated strain of the *Geotrichum* sp. having the international deposit number FERM BP-10300.

6. A method for processing green coffee beans comprising a fermentation step comprising:
   bringing nutritive substances and an isolated microorganism into contact with one another at a temperature of 15 to 30° C. to perform fermentation in the presence of a green coffee bean,
   wherein the isolated microorganism added to the fermentation step is a microorganism belonging to the genus *Geotrichum*,
   wherein the green coffee bean is located within a coffee cherry,
   wherein the nutritive substances include a coffee pulp contained within the coffee cherry, and
   wherein the isolated microorganism belonging to the genus *Geotrichum* is selected from the group consisting of *Geotrichum candidum* (IAM 12700, GEO CA (item no. 200691), GEO CB (items no. 200692), GEO CD1 (item no. 200693), and GEO CE (item no. 200835)), *Geotrichum rectangulatum* (JCM 1750), *Geotrichum klebahnii* (JCM 2171), and a new strain of the *Geotrichum* sp. having the international deposit number FERM BP-10300.

* * * * *